(12) United States Patent
Hendriks et al.

(10) Patent No.: US 11,185,252 B2
(45) Date of Patent: Nov. 30, 2021

(54) DETERMINING A RISK LEVEL POSED BY AN AIR POLLUTANT

(71) Applicant: KONINKLIJKE PHILIPS N.V., Eindhoven (NL)

(72) Inventors: Cornelis Petrus Hendriks, Eindhoven (NL); Cornelis Reinder Ronda, Aachen (DE); Valentina Lavezzo, Heeze (NL); Murtaza Bulut, Eindhoven (NL); Lieke Gertrude Elisabeth Cox, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/592,023

(22) Filed: Oct. 3, 2019

(65) Prior Publication Data

US 2020/0121221 A1 Apr. 23, 2020

Related U.S. Application Data

(60) Provisional application No. 62/747,168, filed on Oct. 18, 2018.

(51) Int. Cl.
| | | |
|---|---|---|
| *A61B 5/08* | (2006.01) | |
| *G16H 50/30* | (2018.01) | |
| *G01N 33/00* | (2006.01) | |
| *A61B 5/11* | (2006.01) | |

(52) U.S. Cl.
CPC ............ *A61B 5/082* (2013.01); *A61B 5/1118* (2013.01); *G01N 33/0067* (2013.01); *G16H 50/30* (2018.01)

(58) Field of Classification Search
CPC ...... A61B 5/082; A61B 5/1118; G16H 50/30; G01N 33/0067
USPC ................................................ 340/573, 573.1
See application file for complete search history.

(56) References Cited

U.S. PATENT DOCUMENTS

| | | | | |
|---|---|---|---|---|
| 9,819,103 | B2* | 11/2017 | Fournier | A41D 1/005 |
| 2007/0148650 | A1* | 6/2007 | Brody | A61B 10/02 |
| | | | | 435/6.14 |
| 2015/0356851 | A1* | 12/2015 | Feletti | H04W 4/023 |
| | | | | 340/539.26 |

(Continued)

FOREIGN PATENT DOCUMENTS

| | | | |
|---|---|---|---|
| KR | 20130098534 A | 9/2013 | |
| WO | 02063539 A1 | 8/2002 | |
| WO | WO-2016193049 A1 * | 12/2016 | A61B 5/1118 |

OTHER PUBLICATIONS

Buonanno, G. et al., 2011, "Tracheobronchial and alveolar dose of submicrometer particles for different population age groups in Italy", Atmospheric Environment, 45(34), pp. 6216-6224.

(Continued)

*Primary Examiner* — Omar Casillashernandez (57) ABSTRACT

A method and system for determining an amount of risk an air pollutant poses to a subject. A risk level is calculated by determining a dosage of the air pollutant, received by the subject over a predetermined period of time, and obtaining historic information about historic dosages of the air pollutant. The risk level is then calculated using the dosage and the historic information to thereby determine a risk level associated with the accumulated deposition of the air pollutant in the portion of the subject's respiratory tract.

14 Claims, 3 Drawing Sheets

(56) References Cited

U.S. PATENT DOCUMENTS

2018/0296123 A1* 10/2018 Karakaya ............... G16H 40/63
2020/0248274 A1* 8/2020 Brody .................. C12Q 1/6886

OTHER PUBLICATIONS

Clifford, S., 2018, "Effects of exposure to ambient ultrafine particles on respiratory health and systemic inflammation in children", Environment International 114, pp. 167-180.

De Backer, J.W. et al., 2008, "Flow analyses in the lower airways: Patient-specific model and boundary conditions", Medical Engineering & Physics 30 (2008) 872-879.

Feng, Y. et al., 2016, "Computational Fluid-Particle Dynamics Modeling for Unconventional Inhaled Aerosols in Human Respiratory Systems", Book chapter from Aerosols—Science and Case Studies, http://dx.doi.org/10.5772/65361.

Lewis, A. and Edwards, P., 2015, "Validate personal air-pollution sensors", Nature Jul. 2016, vol. 535, p. 29-31.

Mazaheri, M. et al., 2014, "School children's personal exposure to ultrafine particles in the urban environment", Environmental Science & Technology (including News & Research Notes), 48(1), pp. 113-120.

Nyarku, M. et al., 2018, "Mobile phones as monitors of personal exposure to air pollution: Is this the future? ", PLoS ONE 13(2): e0193150. https://doi.org/10.1371/journal.pone.0193150.

Poorbahrami, K., 2018, "Regional flow and deposition variability in adult female lungs: A numerical simulation pilot study", Clinical Biomechanics, https://doi.org/10.1016/j.clinbiomech.2017.12.014.

Stingone, J.A., 2017, "Using machine learning to identify air pollution exposure profiles associated with early cognitive skills among U.S. children", Environmental Pollution, vol. 230, 730-740.

Vulovic, A., 2018, "Coupled in silico platform: Computational fluid dynamics (CFD) and physiologically-based pharmacokinetic (PBPK) modelling", European Journal of Pharmaceutical Sciences, vol. 113, pp. 171-184.

W. J. Bair. ICRP publication 66: Human respiratory tract model for radiological protection. Annals of the ICRP, 24 (1-3):1-482, 1994. doi: 10.1016/0146-6453(94)90033-7.

Asgharian, B. Multiple Path Particle Dosimetry Modeling (MPPD) Granular Biopersistent Dust (GBS) and Translational Toxicology: Deriving HECs/Occupational Limit Values. Applied Research Associates, Inc., Berlin, Germany, Dec. 9, 2016.

Asgharian, B. "A multiple-path model of fiber deposition in the rat lung." Toxicological Sciences 44, 80-86. (1998).

* cited by examiner

DETERMINING A RISK LEVEL POSED BY AN AIR POLLUTANT

FIELD OF THE INVENTION

The present invention relates to the field of air pollution monitoring, and in particular to air pollution monitoring for a subject's health.

BACKGROUND OF THE INVENTION

There is a well-established association between exposure to air pollutants, both indoors and outdoors, and impact on a subject's health. In particular, long-term exposure to ultrafine particles (less than 100 nm in diameter) has been identified as contributing to oxidative stress, inflammatory mediator release, and has been linked to other systemic effects such as heart disease and lung disease.

There is a general awareness of the adverse health effects of air pollution, and numerous personal measures to reduce or manage exposure to air pollution have been suggested. These include, for example, the wearing of face masks, the use of air cleaners, avoidance of pollutant sources (such as cooking devices) and lifestyle changes (such as quitting smoking).

However, it has been herein recognized that subjects or persons are not aware of their individual health risks. As a consequence, people are less engaged in managing their respiratory health. The inventors have therefore recognized a desire to provide a personal, objective and quantifiable risk indicator to an air pollutant.

SUMMARY OF THE INVENTION

According to various embodiments described herein, there is provided a method for determining a risk level an air pollutant poses to a subject's health, the method comprising: determining a dosage of the air pollutant received by the subject, the dosage representing an amount of the air pollutant deposited in a portion of the subject's respiratory tract over a predetermined time period; obtaining historic information representative of the amount of the air pollutant cumulatively deposited in the portion of the subject's respiratory tract before the predetermined time period; and calculating a risk level based on the determined dosage of the air pollutant and the historic information, so that the risk level represents an amount of risk to the subject's health resulting from the accumulated deposition of the air pollutant in the portion of the subject's respiratory tract.

Various embodiments described herein may obtain information indicative of the accumulated deposition of a target air pollutant in a portion of the subject's respiratory tract, and calculate a risk level based on this obtained information. In this way, a calculated risk level is based on a predicted accumulated amount of air pollutant deposited in the portion of the subject's respiratory tract.

Various embodiments described herein recognize that there is a relationship between total accumulated amount of air pollutant deposited in a subject's respiratory tract and a risk to their health. The various embodiments described herein therefore proposes to calculate a risk level based on historic information about an accumulated amount deposited on a portion of the subject's respiratory tract.

In this way, a highly accurate and personalized risk level of the subject can be obtained.

It will be understood that the risk level represents a measure or indication of a risk or relative risk that the subject will develop adverse health issues due to the air pollutant. In some embodiments, a risk level represents a measure or indication of a relative risk that the subject will develop a particular disease or adverse condition. A portion of the subject's respiratory tract may comprise the entire respiratory tract or only a part thereof (e.g. the lungs only).

In some examples, a plurality of different risk levels are generated for different diseases and/or conditions (such as oxidative stress). In other words, there may be multiple risk indicators and/or risk levels.

The risk level may be categorical or numerical, for example, an indication of an amount of risk (e.g. HIGH or LOW) or a percentage scale of estimated risk. Preferably, the risk level is a numerical value representing a predicted risk that an air pollutant poses to a subject's health (e.g. a relative risk compared to other subjects, a predicted probability that the subject will suffer from a health problem caused by the air pollutant and so on).

Generating an accurate risk level for the subject enables new information to be provided to the subject, beyond that already available to the subject, and therefore increases an awareness of the subject and thereby a likelihood that the subject's health will be improved. In particular, the risk level provides information related to/relevant to the health status of the subject, which would be a useful tool for diagnosing or treating a patient. The inventors have therefore recognized a technical incentive to enable accurate identification of a risk to the subject's health caused by the accumulated deposition of air pollutants in the portion of the subject's respiratory tract (to improve an understanding of the patient's health status).

The risk level may, for example, be displayed to the subject via a user interface. Thus, the method may comprise a step of displaying the risk level for viewing by the subject or a clinician. Displaying the risk enables the risk level to be provided to the clinician for the purposes of assisting them with the performance of a technical task of diagnosing/treating a patient.

The generated risk level can be dynamic and adaptive, as it reacts to a actual (or predicted) dosage of the subject. In particular, the risk level can be continually updated to reflect changes to the subject's risk (e.g. as their lifestyle changes).

The level of detail of the risk level displayed can vary depending upon the target audience for the risk level. The subject in question may be given a simplified overview of the risk level (for ease of understanding), whilst a clinician may be given a more detailed overview. For example, the view for a subject can include a single score (indicating an overall risk to respiratory health), while a view for the clinician can include a risk score per disease, and may also including the confidence interval for each of these scores.

The step of calculating a risk level based on the determined dosage of the air pollutant and the historic information may comprise: estimating a current accumulative amount of air pollutant deposited in the portion of the subject's respiratory tract at the end of the predetermined period based on the determined dosage of the air pollutant and the historic information; and calculating a risk level based on the estimated current accumulated amount of air pollutant.

Thus, the risk level may be generated based on a current accumulative amount, representing an aggregate or cumulative amount of air pollutant deposited in the portion of the subject's respiratory tract. In other words, the risk level can represent a current risk that the accumulation of air pollutant in the portion of the subject's respiratory tract poses to the subject.

The risk level may, for example, represent a level of risk that the subject will get a particular disease or other adverse condition (e.g. oxidative stress). A plurality of risk levels may thereby be generated, each representing a risk to a different disease and/or other adverse condition.

The step of calculating a risk level based on the determined dosage of the air pollutant and the historic information optionally comprises predicting a future accumulative amount of air pollutant deposited in the portion of the subject's respiratory tract at a future point in time, based on the determined dosage of the air pollutant and the historic information; and calculating a risk level based on the predicted future accumulated amount of air pollutant.

Thus, an estimate or prediction of a future accumulated amount of the air pollutant in the portion of the subject's respiratory tract can be made. This estimate may be processed to calculate a risk level to the subject, representing a future risk to their health (e.g. if they continue their current lifestyle). This may enable more appropriate determination and representation of their future health status.

Alternatively, or in addition, different risk level estimates for different future lifestyle can be also generated. Thus, a risk level for different scenarios of the subject's future actions may be generated. In this way, the subject may be able to better understand the potential effects of different lifestyles (or lifestyle changes).

The step of calculating a risk level may comprise: modelling an accumulated amount of air pollutant deposited in the respiratory tract of the subject over time using the determined dosage of the air pollutant and the historic information; and using the model to determine a risk level of the subject.

Modelling an accumulated amount of air pollutant allows a pattern of accumulation to be determined. By using a pattern or model of the accumulated amount of air pollutant deposited in the portion of the subject's respiratory tract, a more accurate assessment of the subject's risk to the air pollutant can be determined.

The step of calculating a risk level may comprise obtaining comparative amount information representing the accumulated amount of the target air pollutant in at least one other subject; and determining a risk level of the subject further based on the comparative amount information.

In this way, the risk level may be a relative risk comparative to other members of the population. This enables an intuitive, quantifiable and easily-understandable level of risk to be determined.

Preferably, the step of determining a dosage of the air pollutant comprises: determining an inhalation and/or exhalation flow rate of the subject; obtaining a pollution level representative of an amount of the air pollutant in the air inhaled by the subject during the predetermined time period; obtaining a model of the portion of the subject's respiratory tract; and determining a dosage of the air pollutant deposited in the portion of the subject's respiratory tract over the predetermined time period based on the inhalation and/or exhalation flow rate, the pollution level and the model of the portion of the subject's respiratory tract.

The various embodiments described herein effectively recognizes that dosage models (e.g. designed for determining dispersal of aerosols from nebulizers), can be exploited to determine a dosage of air pollutant in the portion of the subject's respiratory tract. Using a model of the portion of the subject's respiratory tract enables a highly accurate measurement of the dosage of the air pollutant deposited in the portion of the subject's respiratory tract to be obtained.

By improving an accuracy of determining a dosage of the air pollutant inhaled by the subject during the predetermined time period, an accuracy of determining a risk level of the subject can also be improved.

In some embodiments, to determine the dosage, a length of the predetermined time period must also be provided.

The step of obtaining a pollution level may comprise: determining a location of the subject; obtaining, based on the location of the subject, air pollution data indicative of an amount of the air pollutant in outdoor air at the location of the subject; obtaining environment information indicative of one or more characteristics of an environment in the vicinity of the subject; and modifying the air pollution data based on the environment information to thereby determine an environment-specific pollution level representative of an amount of the air pollutant in the air inhaled by the subject.

Outdoor air pollution data is readily accessible to the general public. However, it has been recognized that such data may not accurately represent an amount of pollution in the immediate environment of the subject.

The various embodiments described herein therefore proposes to obtain environment information, indicative of an environment in the vicinity of the subject (e.g. whether the subject is indoors, the presence of pollutant sources and so on). This information can be used to modify the modeled amount of air pollutant in outdoor air (e.g. revise upwards or downwards) to determine an environment-specific pollution level. This increases an accuracy of determining an amount of air pollutant deposited in the portion of the subject's respiratory tract, and thereby an accuracy of determining a risk level to the subject.

In some embodiments, the step of determining an inhalation and/or exhalation flow rate comprises: determining a lung capacity of the subject; determining a respiration rate of the subject; and determining an inhalation flow rate based on the lung capacity and respiration rate of the subject.

The respiration rate of the subject may, for example, be obtained from a mobile device associated with the subject. For example, a microphone may record the breathing of the subject or an accelerometer of a mobile device may measure movement of the subject's chest. In yet other examples, a camera (of the mobile device) may be used to record a movement of the subject's chest and thereby measure the subject's respiration rate.

The proposed method enables an inhalation flow rate to be accurately identified, which increases an accuracy of determining an amount of air pollutant deposited on the portion of the subject's respiratory tract over the predetermined time period, and thereby the accuracy of determining a risk level to the subject's health.

The step of determining an inhalation and/or exhalation flow rate may comprise: obtaining sensor data from a mobile device associated with the subject; determining an activity performed by the subject based on the sensor data; and determining an inhalation flow rate based on the determined activity performed by the subject.

It has been recognized that an inhalation/exhalation flow rate can be accurately estimated by determining an activity performed by the subject (e.g. running, walking, sleeping, cycling and so on). In particular, a level of exertion provided by the subject can be used to estimate the inhalation/exhalation flow rate of the subject. It will be appreciated that typically the greater the level of exertion, the greater the inhalation/exhalation flow rate of the subject.

Sensor data of a mobile device associated with the subject, such as accelerometer data or location information, can be processed to determine an activity performed by the subject.

In other example, an exertion rate can be derived from heart-rate measurements and/or accelerometer data, and used to determine an inhalation/exhalation flow rate of the subject. Heartrate measurements or accelerometer data may be obtained, for example, from a mobile device and/or a Photoplethysmogram (PPG)-based device, such as smart watch with an inbuilt pulse oximeter.

In some examples, determining an inhalation and/or exhalation flow rate is further based on characteristics of the subject, such as age, gender and so on. It has been recognized that there is a relationship between such characteristics of the subject and an inhalation/exhalation flow rate of the subject. Thus, accuracy of determining an inhalation/exhalation flow rate can be improved.

In at least one embodiment, the step of obtaining a model of the portion of the subject's respiratory tract comprises obtaining a multiple-path particle dosimetry model of the portion of the subject's respiratory tract; and the step of determining a dosage of the air pollutant deposited in the portion of the subject's respiratory tract over the predetermined period of time comprises using the multiple-path particle dosimetry model to process the inhalation and/or exhalation flow rate and pollution level to thereby determine a dosage of the air pollutant deposited in the portion of the subject's respiratory tract over the predetermined period of time.

The method may further comprise generating a risk mitigation strategy for the subject based on at least determined dosage of the air pollutant and the historic information, so that a generated risk mitigation strategy represents a strategy for reducing a risk caused by the accumulation of the air pollutant in the portion of the subject's respiratory tract.

The method may comprise a step of displaying the risk level to the subject.

According to examples in accordance with various embodiments described herein, there is also provided computer program comprising code means for implementing any herein described method when said program is run on a computer.

According to various embodiments described herein, there is provided a system for determining a risk level an air pollutant poses to a subject's health. The system comprises an obtaining unit adapted to determine a dosage of the air pollutant received by the subject, the dosage representing an amount of the air pollutant deposited in the portion of the subject's respiratory tract over a predetermined time period; and obtain historic information representative of the amount of the air pollutant cumulatively deposited in the portion of the subject's respiratory tract before the predetermined time period. The system also comprises a risk calculation unit adapted to calculate a risk level based on the determined dosage of the air pollutant and the historic information, so that the risk level represents an amount of risk to the subject's health resulting from the accumulated deposition of the air pollutant in the portion of the subject's respiratory tract.

In an embodiment, the obtaining unit is adapted to estimate an current accumulative amount of air pollutant deposited in the portion of the subject's respiratory tract at the end of the predetermined period based on the determined dosage of the air pollutant and the historic information; and the risk calculation unit is adapted to calculating a risk level based on the estimated current accumulated amount of air pollutant.

These and other aspects will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The various embodiments will be described with reference to the Figures.

It should be understood that the detailed description and specific examples, while indicating exemplary embodiments of the apparatus, systems and methods, are intended for purposes of illustration only and are not intended to limit the scope of the various embodiments described herein. These and other features, aspects, and advantages of the apparatus, systems and methods will become better understood from the following description, appended claims, and accompanying drawings. It should be understood that the Figures are merely schematic and are not drawn to scale. It should also be understood that the same reference numerals are used throughout the Figures to indicate the same or similar parts.

According to various embodiments described herein, there is proposed a method and system for determining an amount of risk an air pollutant poses to a subject. A risk level is calculated by determining a dosage of the air pollutant, received by the subject over a predetermined period of time, and obtaining historic information about historic dosages of the air pollutant. The risk level is then calculated using the dosage and the historic information to thereby determine a risk level associated with the accumulated deposition of the air pollutant in the portion of the subject's respiratory tract.

Embodiments are at least partly based on the realization that increased accumulation of an air pollutant in a subject's respiratory tract causes increased risk to a subject's health (caused by the air pollution), and in particular to a respiratory health. The inventors have also recognized a need or desire for determining or quantifying a risk posed to a subject's health by the air pollutant. Embodiments propose to use information indicative of an accumulated amount of air pollutant deposited in the portion of the subject's respiratory tract to generate an indicator of the risk posed by the air pollutant (i.e. the risk level).

Illustrative embodiments may, for example, be employed in mobile devices held, carried or worn by the subject. Such a mobile device may be able to monitor a (current) dosage of air pollutant received by the subject, and continually update the subject as to a risk to their health.

As used herein, the term "respiratory tract" refers to the parts of the subject's body that contribute to the process of respiration, including the lungs (e.g. bronchi, bronchioles and trachea), larynx, nasal cavity and so on. Thus, a portion of the respiratory tract refers to a combination of any one more of such parts. "Air pollutant" refers to a substance or particle present in inhaled air that can cause harm or irritation to a subject/person, such as allergens, ultrafine particles, volatile organic compounds (VOCs), carbon dioxide ($CO_2$), sulfur dioxide ($SO_2$) and so on.

The term "amount of the air pollutant" refers to any measure of the quantity of air pollutant deposited in a portion of the subject's respiratory tract, including a mass, volume, surface area and/or particle count.

Hereafter proposed methods and embodiments are particularly advantageous when employed in a mobile device for carrying/holding/wearing by a subject. As used herein, the term "mobile device" refers to any wearable, portable or holdable device capable of obtaining sensor data concerning the subject. Examples of mobile devices include: smart phones, smart watches, pedometers, face masks, vital sign patches, cameras, and so on.

Hereafter described embodiments refer to the subject's entire respiratory tract, but may be adapted for use with any portion of the subject's repistoraty tract (e.g. only the lungs).

Figure 1:
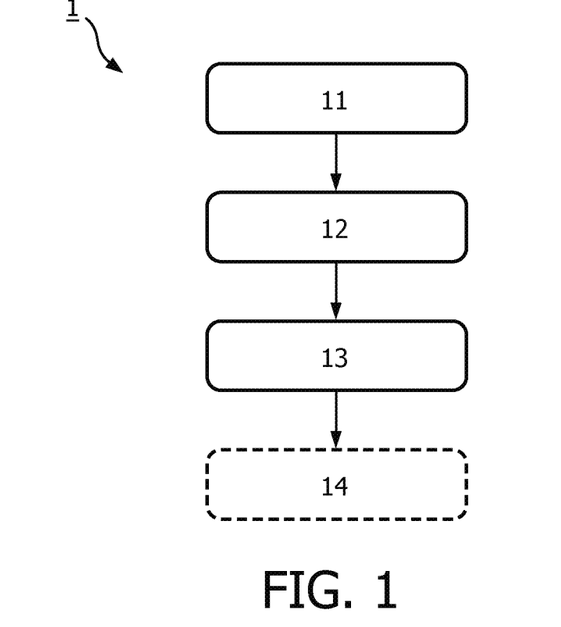
FIG. 1 illustrates a method of determining a risk level according to an embodiment.

FIG. 1 illustrates a method 1 of determining a risk level to a subject's health.

The method 1 comprises a step 11 of determining a dosage of air pollutant representative of an amount of a target air pollutant deposited in the subject's respiratory tract over a predetermined time period (i.e. a "dosage"). Thus, step 11 determines an amount of a target air pollutant (e.g. ultrafine particles) that are deposited in the subject's respiratory tract over a period of time.

The amount of air pollutant deposited in the subject's respiratory tract over a predetermined time period may, for example, be referred to as a "dose" or "dosage" of air pollutant. The predetermined time period may, for example, be a single breath of the subject or may span a longer period of time, e.g. a minute, hour, day or week. The predetermined period of time is less than the lifetime of the subject. The dosage may be a predicted dosage of the air pollutant (e.g. by applying a model to certain characteristics) or a measured dosage of the subject (e.g. by actively measuring deposition in the subject's respiratory tract).

The method 1 then moves to a step 12 of obtaining historic information that represents an amount of the air pollutant deposited in the subject's respiratory tract before the predetermined time period. Thus, the historic information represents an accumulated amount of the target air pollutant deposited in the subject's respiratory tract before the predetermined time period begins.

The method then moves to a step 13 of calculating a risk level to a subject's health posed by the air pollutant (i.e. the target air pollutant). In particular, step 13 comprises processing the determined dosage of air pollutant (from step 11) and the historic information (from step 12) to determine a risk level to the subject's health.

Step 13 exploits the herein recognized understanding that there is a relationship between a risk level to the subject and accumulated deposition of the target air pollution in the subject's respiratory tract. Thus, by processing a determined amount of air pollutant inhaled by the subject (i.e. the dosage), together with historic information, an accurate measure of the subject's risk can be determined.

Thus, step 13 preferably comprises estimating an accumulated amount of the target pollutant deposited in the subject's respiratory tract at the end of the predetermined period ("current accumulated amount") based on the dosage and the historic information, and determining a risk level to the subject's health resulting from the current accumulated amount.

The method may further comprise optional step 14 of providing the calculated risk level to a subject via a user interface. This ensures that the subject is made aware of a calculated risk level.

In at least one example, information on the dosage and/or the current accumulated amount are stored in health data (e.g. a medical record) of the subject. This may be used for future iterations of performing the method (e.g. as historic information).

Embodiments are particularly advantageous when the air pollutant comprises ultrafine particles, as the inventors have recognized that a strong relationship exists between an amount of ultrafine particles deposited in a subject's respiratory tract and a subject's risk to adverse health issues.

The proposed method therefore enables a subject-specific risk level to be identified based on information indicative of an accumulated amount of pollutant deposited in the subject's respiratory tract.

Hereafter, references to a "dosage" refers to an amount (or estimate thereof) of the air pollutant deposited in a subject's respiratory tract during a predetermined period of time (e.g. a single breath of the subject). References to "accumulated amount" refer to a cumulative, aggregate or accumulative amount (or estimate thereof) of air pollutant deposited in a subject's respiratory tract from the subject's birth to a particular point in time, e.g. the end of the predetermined period of time. The "accumulated amount" can be considered to be a sum of dosages (i.e. a total or overall dosage). The "current accumulated amount" refers to an accumulated amount at the end of the predetermined period of time.

Preferably, the historic information obtained in step 12 is a measure or indication of the (e.g. estimated) accumulated amount of the air pollutant deposited in the subject's respiratory tract before or at the start of the predetermined period (i.e. a "historic accumulated amount"). The historic information may be obtained by estimating an accumulated amount of air pollutant deposited in the subject's respiratory tract before the predetermined time period.

Preferably, the historic information provides a historic accumulated amount $M_{HA}$ that indicates a cumulative amount of the target air pollutant deposited in the subject's respiratory tract over the subject's lifetime up to the start of the predetermined period.

Purely by way of example, estimation of a historic accumulated amount $M_{HA}$ may be performed by using an age "Age" of the subject, the dosage or current amount $M_C$ determined in step 11 and the length $t_{pd}$ of the predetermined time period. The following equation may be applied to estimate an accumulated amount $M_{HA}$ ("historic accumulated amount") of the deposited air pollutant before or at the start of the predetermined time period. The historic accumulated amount represents an amount of the air pollutant deposited in the subject's respiratory tract before the beginning of the predetermined period.

$$M_{HA} = \frac{Age}{t_{pd}} \cdot M_C \qquad (1)$$

In another example, a historic accumulated amount of the deposited air pollutant in the subject's respiratory tract may be estimated based on questionnaire data provided by the subject (e.g. indicating past locations of living, smoking status, historic exercise information and so on). The questionnaire data may be processed to estimate a historic accumulated amount, e.g. by comparing to known examples of questionnaire data and historic accumulated amount. Determining the historic accumulated amount may comprise using a machine learning algorithm to process the questionnaire data, where the machine learning algorithm is trained to establish links between questionnaire data and historic accumulated amounts. The historic information may therefore comprise questionnaire data.

Of course, in some embodiments information on historic measures of the amount deposited in the subject's respiratory tract ("historic dosages") or historic estimates of an accumulated amount deposited in the subject's respiratory tract may be available ("historic accumulated amounts"), e.g. from previous iterations of the proposed method. This information may be processed to improve a determination of a historic accumulated amount $M_{HA}$ for the subject at a beginning of the predetermined period.

In one example, a plurality of dosages of air pollutant are obtained over a period of time (i.e. a dosage received by a subject is tracked), such as over the course of a day or week. A model (e.g. best fit curve) can then be applied to the plurality of dosages. Using the model, estimates of historic dosages can be calculated, e.g. via extrapolation based on the subject's age or using a machine learning algorithm. The estimated historic dosages can thereafter be summed in order to obtain a historic accumulated amount. Thus, the historic information may be derived from the dosage (or plurality of dosages) obtained in step 11.

Generally speaking, the historic information should be sufficient to enable calculation or estimation of a cumulative amount of air pollutant deposited in the subject's respiratory tract at the start of the predetermined period.

Step 13 may comprise combining (e.g. summing) the historic accumulated amount $M_{HA}$ and the dosage $M_C$ determined in step 11 to determine/estimate a current accumulated amount $M_{CA}$, which represents an accumulated amount of the air pollutant deposited in the subject's respiratory tract at the end of the predetermined time period (i.e. over the subject's known lifetime). Step 13 may then comprise determining the risk level based on the current accumulated amount $M_{CA}$.

Thus, by tracking a dosage $M_C$ of the target air pollutant received by the subject, a current accumulated amount $M_{CA}$ of the air pollutant deposited in the subject's respiratory system can also be tracked.

The dosage $M_C$ should be distinguished from the current accumulated amount $M_{CA}$. The dosage $M_C$ represents an amount of the air pollutant deposited in the subject's respiratory tract from a start of the predetermined time period to an end of the predetermined time period. The current accumulated amount $M_{CA}$ represents an amount of the air pollutant deposited in the subject's respiratory tract from the subject's birth until an end of the predetermined time period. The end of the predetermined time period may represent a current point in time.

In other examples, step 13 may comprise predicting a future accumulated amount $M_{FA}$, which represents a predicted cumulative amount of the air pollutant deposited in the subject's respiratory tract at a future point in time (i.e. beyond the end of the predetermined period). This may be performed, for example, by extrapolating beyond the current accumulated amount $M_{CA}$, e.g. based on the subject's age. This future accumulated amount $M_{FA}$ may be used to determine a risk level of the subject.

In some embodiments, the step of predicting a future accumulated account $M_{FA}$ is further based on possible lifestyle modifications to the subject (e.g. which may affect an amount of pollutant to which they are exposed). For example, a first predicted future accumulated amount may be based on an assumption that no changes are made to the subject's lifestyle, whereas a second future accumulated amount may be based on an assumption that some changes are made to the subject's lifestyle (e.g. wearing of a face mask to reduce exposure to pollutant).

In some embodiments, a plurality of different future accumulated amounts $M_{FA}$ may be generated, representing different possible scenarios (e.g. different lifestyle changes) for the subject. Each of the plurality of different future accumulated amounts may be separately processed to determine a risk level of the subject in different scenarios.

In this way, a plurality of different risk levels may be generated representing different predicted future accumulated amounts of pollutant.

In a preferred embodiment, step 13 comprises modelling an accumulated amount of air pollutant deposited in the respiratory tract of the subject over time using the determined dosage and the historic information. This model may then be used to determine a risk level of the subject.

In particular, a model may represent a prediction of how the accumulated amount of air pollutant deposited in the subject's respiratory tract changes over time (e.g. from birth to a present point in time or from birth to a future point in time). The model may then be used to determine a risk level of the subject.

A model can be generated using the dosage and the historic information. For example, the historic information may provide previous estimates of a total accumulated amount of air pollutant deposited in the subject's respiratory tract ("historic accumulated amounts"). A curve fitting algorithm may be used to identify a mathematical function that best fits the historic accumulated amounts (and optionally the current accumulated amount) to thereby determine a model representing how the cumulative amount of air pollutant deposited in the subject's respiratory tract changes over time.

It will be appreciated that such a model may be used to predict a future accumulated amount $M_{FA}$ of the subject (e.g. via extrapolation). Of course, the model may be modified based-on possible changes to the subject's lifestyle (e.g. wearing of a facemask).

In some embodiments, the historic accumulated amount and/or the dosage may be modified based on smoking information of the subject (e.g. input by the subject via a user interface). In particular, smoking information may indicate a number of cigarettes smoked by the subject (e.g. per day or over a predetermined period of time). This may provide an offset in the historic accumulated amount and/or the dosage, in particular increasing the size of the accumulated amount and/or dosage.

Figure 2:
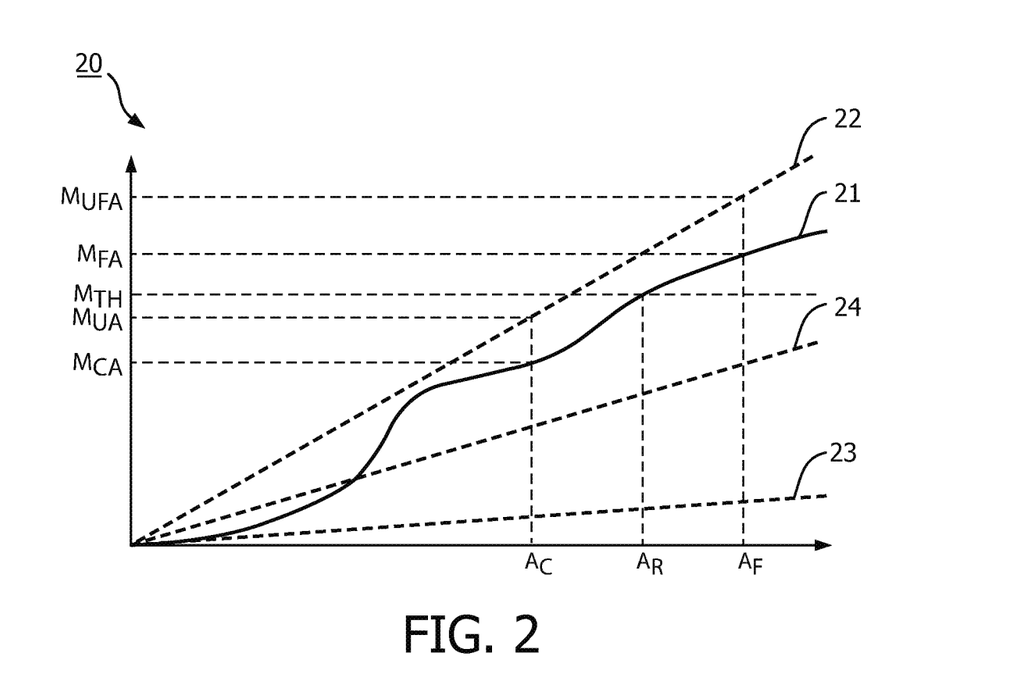
FIG. 2 is a graph illustrating an amount of deposited air pollutants in a subject's respiratory tract over time.

FIG. 2 is a chart 20 illustrating a model 21 of the subject's accumulated amount of air pollutant over time. The x-axis represents an age of the subject (e.g. spanning from 0 to 80 years in age), and the y-axis represents an accumulated amount of deposited air pollutant in the subject. A current accumulated amount $M_{CA}$ (i.e. for a current age $A_C$ of the subject—i.e. at the end of the predetermined time period) is also illustrated for the sake of clarity.

FIG. 2 can be used to understand various embodiments for determining a subject's risk level posed by the air pollutant.

In a first example, the risk level may indicate a predicted number of years (or other length of time) until a dangerous or threshold accumulated amount $M_{TH}$ of air pollutants is reached ("threshold accumulated amount"). The threshold accumulated amount $M_{TH}$ may, for example, represent an accumulated amount of the air pollutant deposited in the subject's respiratory tract that is associated with a high probability (e.g. greater than a predetermined threshold) that the subject will suffer from an air pollutant-based disease or other adverse effect/condition, such as oxidative stress. The threshold accumulated amount $M_{TH}$ can be used to determine a predicted risk age of the subject $A_R$ (i.e. an age at which they will reach the threshold accumulated amount $M_{TH}$). The risk level may indicate a difference between the current age $A_C$ of the subject and the predicted risk age $A_R$ of the subject. In another example, the risk level simply indicates the risk age $A_R$ of the subject.

In a second example, a risk level may indicate a relative risk of the subject, e.g. compared to other members of the population. It has been recognized that increased accumulated respiratory tract deposition of the air pollutant leads to an increased health risk. Thus, by providing a relative assessment of risk to other members of the population, a relative risk to the subject's health can be quantified.

In the second example, the relative risk may represent a relative difference between a current accumulated amount $M_{CA}$ of the subject and a corresponding accumulated amount $M_{UA}$ for an "unhealthy" subject of the same age $A_C$ (the unhealthy subject having a corresponding model 22). The risk level may be presented as a percentage. By way of example, the relative risk may indicate that the current accumulated amount $M_{CA}$ is a certain percentage (e.g. 80%) of the corresponding accumulated amount $M_{UA}$ for the "unhealthy" subject. Here, an unhealthy subject may be one whose accumulated amount is in the top 10% or 5% of a population of subjects, and may be represented by an average of such "unhealthy" subjects.

In a modified version of the second example, the relative risk may represent a relative difference between a future (predicted) accumulated amount of the subject $M_{FA}$ and a corresponding accumulated amount $M_{UFA}$ of an unhealthy subject (e.g. of the same age $A_F$ as the subject at the point in the future).

More than one risk value may be obtained (e.g. to identify a current risk and a predicted future risk, which could indicate that a risk may change over time).

Of course, the second example may be adapted to instead or additionally compare the subject to a "healthy" person (e.g. having model 23), e.g. whose accumulated amount is in a bottom 10% or 5%, or an "average" person (e.g. having model 24).

In a third example, the risk level may indicate which percentile (e.g. top 10%, top 20%, bottom 10% and so on) of a population the subject falls into. This may, for example, comprise comparing a current accumulated amount $M_{CA}$ of the subject, or a predicted future accumulated amount $M_{FA}$ to corresponding accumulated amounts for other subjects at a same age $A_C$, $A_F$.

Population information (e.g. for the second or third examples) may be obtained from a remote server (such as a cloud-based server) processing aggregate information on population accumulative amount. Embodiments of the method may therefore comprise passing information of a current accumulated amount MAC (or other amount-based information) to a remote server for processing to form population information. In other examples, inhaled amount profiles of different types of persons can be available as static information when initiating the method (e.g. installing an application).

In yet examples, a risk level may be calculated using an algorithm or formula. By way of example only, one possible formula could have the following form:

$$R = M \cdot DR \qquad (1)$$

where R is the risk level, M is the (current or future) accumulated amount of pollutant, and DR is a dose response factor representing a relationship between a dose of a particular pollutant and a health response (e.g. occurrence of a disease or other adverse condition, e.g. cancer of oxidative stress).

In yet another example, a risk level may be calculated using a machine learning model. The machine learning model can define a relationship between (current or future) accumulated amount and risk level.

Methods of generating a machine learning model will be well known to the skilled person. Typically, this comprises obtaining training data comprising example input data (here: accumulated amount) and example output data (here: risk level), generating estimated output data by processing the example input data with a machine learning model (e.g. initialized with random parameter values) and modifying the machine learning model to minimize the difference between the estimated output data and the example output data.

In some examples, a risk level may be determined further based on subject information (such as health data of the subject). In particular, a determined risk level may be modified based on the subject information, such as an indication of sensitivity to the target air pollutant or a family history of sensitivity to the target air pollutant. Thus, in an example, a numerical risk level may be upwardly revised in response to an indication that the subject is or could be sensitive to the target air pollutant, or already suffers from respiratory conditions such as asthma. Health data may include, for example, past medical history (which could affect a historic and/or current amount of pollutant inhaled by the subject) or a current health status of the subject (which could affect an amount of pollutant deposited in the subject's respiratory tract).

For example, health data of the subject may define a "revision factor" that indicates how a determined risk level is to be revised. For example, it is recognised that AAT deficiency or low weight at birth increases the risk of developing COPD. So, if it is known from a person's health data that a person has increased risk factors (e.g. from their history), then the relative risk may revised upwardly by a numerical factor (e.g. any real number, such as any number greater than 1, e.g. 2 or more). This may ensure that the relative risk is more accurately and appropriately assessed for the person, i.e. it is more personalised.

Other health data may include a subject's smoking status or smoking information (e.g. how many cigarettes the subject smokes), which would affect the risk level to the subject. This may also affect or contribute to the numerical factor discussed above.

In another example, health data of the subject may affect a value of the dosage of the pollutant on the subject's respiratory tract (e.g. as having a cough would cause the subject to inhale more air and thereby more pollutant).

The "revision factor" might be estimated more accurately using a machine learning model (which process health data to identify a revision factor).

Figure 3:
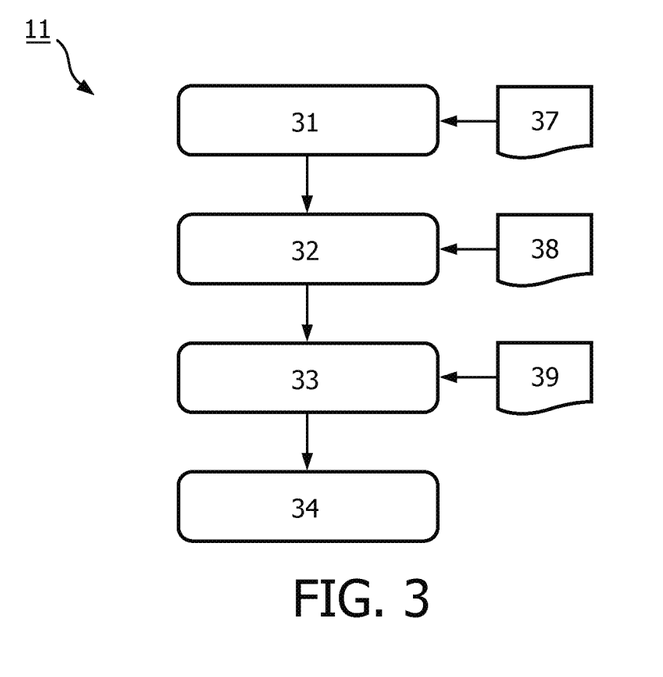
FIG. 3 illustrates a method of determining an amount of deposited air pollutants for an embodiment of the invention.

FIG. 3 illustrates a method 11 for determining an amount of the air pollutant deposited in the subject's respiratory tract over a predetermined time period, i.e. the "dosage".

The method comprises a step 31 of determining an inhalation flow rate of the subject. The method then moves to a step 32 of obtaining a pollution level representative of an amount of the air pollutant in the air inhaled by the subject during the predetermined time period. The method then performs step 33 of obtaining a model of the subject's respiratory tract.

The method further comprises a step 34 of determining an amount of the air pollutant deposited in the subject's respiratory tract over the predetermined time period based on the inhalation flow rate, the pollution level and the model of the subject's respiratory tract. In this way, step 34 determines a dosage of the air pollutant received by the subject.

In other words, step 34 comprises using the model of the subject's respiratory tract to identify a dosage of air pollutant, where the dosage represents an amount of the air pollutant deposited in the subject's respiratory tract over a predetermined period of time (e.g. a single breath). In particular, the model can process the inhalation flow rate and the obtained pollution level to determine an amount of air pollutant deposited in the subject's respiratory tract over a predetermined period of time.

Examples of suitable models include a simple ID model (such as the ICRP Human Respiratory Tract Model for Radiological Protection) or more complex 3D models (such as a multiple-path particle dosimetry model) that require information of the geometry of the subject's respiratory tract. The process performed in step 34 will differ depending upon the model of the subject's respiratory tract obtained in step 33, and would be well understood by the skilled person.

By way of example, a multiple-path particle dosimetry model (MPPD) can calculate the deposition of monodisperse and polydisperse aerosols (e.g. pollutants in air) in the respiratory tract of a subject. In particular, a single-path and/or multiple-path method may be used to track air flow through a lung geometry and calculate pollutant deposition. The lung geometry may, for example, be a representative lung geometry (e.g. one determined based on patient characteristics, such as age, gender and so on) or a patient-specific lung geometry.

A patient-specific lung geometry of the subject's respiratory tract may be obtained or derived from one or more medical images of the subject (such as CT scans) by constructing a 3D model of the subject's respiratory tract. A subject-specific 3D flow simulation using the obtained 3D model of the subject's respiratory tract may be performed, using the inhalation flow rate and the obtained pollution level to determine a dosage of the air pollutant received by the subject during a predetermined time period. By performing a subject-specific 3D flow simulation, a more accurate assessment of the dosage received by the subject can be determined.

In particular, a dosage can be determined by integrating an amount of pollutant deposited per surface element of the lung geometry (e.g. performing an integration comprising both time and area with respect to the lung geometry).

By way of another example, a one-dimensional model of the subject's respiratory tract may be used to calculate the dosage. An example of a suitable one-dimensional model is disclosed in W. J. Bair. ICRP publication 66: Human respiratory tract model for radiological protection. Annals of the ICRP, 24 (1-3): 1-482, 1994.

Other models for determining a dosage, i.e. an amount of air pollutant deposited in the subject's respiratory tract during a predetermined period of time such as a single breath or a day, would be readily apparent to the skilled person.

Different example embodiments of step 31 are hereafter described. By way of reminder, step 31 comprises determining an inhalation flow rate of the subject (during the predetermined time period).

In a first example, step 31 may comprise estimating an inhalation flow rate from a look-up table which relates activity/exertion (and optionally age group) of a subject to an inhalation flow rate. In other words, step 31 may comprise determining an activity performed or exertion provided by a subject, and looking up a corresponding inhalation flow rate in a look-up table. Determining an activity/exertion performed may, for example, comprise obtaining sensor data from a mobile device held/worn by the subject and determining an activity/exertion based on the sensor data. For example, location information may be used to determine a speed of the subject, to thereby establish what activity the subject is performed (e.g. sports, running, walking etc.). In other examples, the activity information is obtained by receiving an input from the subject, e.g. via a user interface.

In a second example, step 31 comprises obtaining a lung capacity, e.g. tidal volume, of the subject (e.g. previously measured during a physician visit or estimating from a fitness test, patient characteristics or a video of the subject's breathing) and determining a respiration rate of the subject. The inhalation flow rate can be calculated by multiplying the lung capacity by the respiration rate. The respiration rate may be obtained, for example, from a mobile device associated/held/worn by the subject. In particular, accelerometer, video or microphone data may be processed to determine a respiration rate. To account for a situation in which the subject does not carry the mobile device all day, missing data can be interpolated or estimated from historical data (similar days).

In a third example, the inhalation flow rate can be estimated by obtaining a video of at least the subject's chest whilst breathing during the predetermined time period. A lung capacity of the chest can be estimating by determining a difference between the volume of the chest at exhalation and a volume of the chest at inhalation, and a respiratory rate can be identified. The inhalation flow rate can be calculated by multiplying the lung capacity by the respiration rate.

In a fourth example, the inhalation flow rate can be estimated by using an exhalation flow rate of the subject (e.g. as obtained using any previously described method for determining an inhalation flow rate). This is because there may be a known relationship between the inhalation and exhalation flow rate of a subject. Thus, step 31 may comprise obtaining an exhalation flow rate, and using this as a basis for the inhalation flow rate.

Different example embodiments of step 32 are hereafter described. By way of reminder, step 32 comprises obtaining a pollution level representative of an amount of the air pollutant in the air inhaled by the subject during the predetermined time period. The pollution level may, for example, be a concentration (e.g. parts per million) of a target air pollutant in the air.

In a first example, step 32 comprises determining a pollution level from a pollution sensor in the vicinity of the subject, such as from a mobile device held/carried by the subject or an air cleaning device in the vicinity of the subject.

In a second example, step 32 comprises determining a pollution level from a pollutant source in the vicinity of the subject, such as an air fryer, capable on providing information indicative of an amount of pollutant produced. For example, a pollution level in the vicinity of the subject may depend on the food that has been cooking in the nearby environment. Thus, by communicating with a pollutant source such as an air fryer, a pollution level in the air inhaled by the subject can be estimated.

In a third example, step 32 comprises identifying a location of the subject (e.g. via a mobile device held/carried by the subject) and determining a pollution level based on the subject's location. Pollution data of outdoor air for different locations is widely available, e.g. from the internet or other data sources. The location of the subject can be cross referenced to the pollution data to identify a pollution level of outdoor air, which may be used to represent the pollution level obtained in step 32.

The third example may be further modified to comprise a further step of obtaining environment information indicative of characteristics of the environment in the vicinity of the subject. The pollution level of outdoor air can be modified to take account of the environment information. Thus, an environment-specific pollution level representative of an amount of the air pollutant in the air inhaled by the subject can be calculated. Environment information may, for example identify a location, nearby objects or known activities in the nearby environment that can affect the pollution level.

For example, an indoors/inside location will have a reduced pollution level (compared to an outdoor/outside location). A nearby air purifier will also decrease the pollution level (compared to an outdoor location). If it is known that cooking takes place in the subject's location, then a pollution level will be increased (as cooking produces ultrafine particles or other pollutants).

The environment information may be obtained, for example, by processing an image or video taken by the subject to identify objects in the nearby surroundings that may affect a pollution level (e.g. via image recognition). Alternatively, the environment information may be obtained by receiving an input from the subject (e.g. via a user interface) or from communications from nearby devices (such as an air purifier adapted to provide communications).

Figure 4:
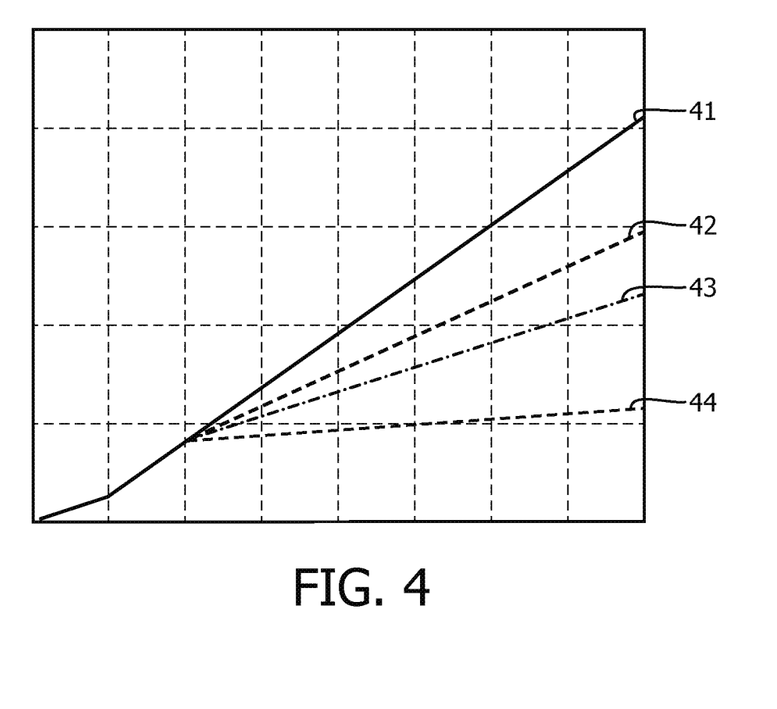
FIG. 4 illustrates different predictions for a future accumulated amount of air pollutants deposited in a subject's respiratory tract.

FIG. 4 can be used to explain examples of how to predict different future accumulated amounts, from which different risk values may be calculated.

In particular, FIG. 4 demonstrates the effect of interventions (i.e. lifestyle changes) on the predicted accumulated amount of pollutant (here: mass of PM2.5). The diagram is based on a male subject at the age of 20. The graph below shows the effect of four different scenarios: "no intervention" 41 (i.e. no lifestyle changes), "indoor air purification" 42 (i.e. where indoor air purification is provided to the subject), "face mask" 43 (i.e. where the subject wears a face mask when in a polluted outdoor situation), and a combination 44 of the two interventions.

The interventions can reduce the accumulated amount in the remaining life of the subject by a factor 10 (when the combination 44 approach is taken).

In this simple example the accumulated amount M within a predetermined time period may be calculated as follows:

$$M = C \cdot B \cdot T \cdot DF \quad (1)$$

where C is the mass concentration of the air pollutant (in kg/m$^3$), B is the inhalation flow rate of the subject [m$^3$/s] (which, as later explained, may depend on the activity level, gender, age of the subject etc.), T is the length of the predetermined time period (in seconds s), and DF is the deposition fraction [−], representing a proportion of the mass concentration that is deposited in the small airways and the alveoli combined, e.g. as calculated using ICRP Human Respiratory Tract Model for Radiological Protection.

The accumulated mass within the predetermined time period represents the dosage of the air pollutant received by the subject (e.g. up to a current or future point in time). This may, for example, be added to a known or historic accumulated mass of pollutant (e.g. of the subject at 20 years of age), to produce a total accumulated mass of pollutant.

In other words, the predicted amount of deposited pollutant is determined based on the inhalation flow rate (B), the pollution level (C), the model of the subject's respiratory tract (DF) and the length of a predetermined period of time.

It will be appreciated that multiple different values for the inhalation flow rate and/or pollution level may be used to calculate the predicted amount of deposited pollutant, to account for different environments encountered by the subject or actions performed by the subject during the predetermined period of time.

By way of example only, the following values may be used.

Mass concentrations C of the inhaled air (particle diameter 2.5 micrometer): Indoor (w/o intervention): 100 microgram/m$^3$; Indoor (air purifier): 10 microgram/m$^3$; Outdoor (w/o intervention): 100 microgram/m$^3$; and Outdoor (with face mask)=10 microgram/m$^3$.

Inhalation flow rate B of a male adult person: sleep: 1.25 E-4 m$^3$/s; sitting, awake: 1.5 E-4 m$^3$/s; light exercise: 4.17 E-4 m$^3$/s; heavy exercise: 8.33 E-4 m$^3$/s. Between the ages of 0-10 years the inhalation rate can be assumed to be half the inhalation rate of an adult person.

Time periods of activities (average week day): 8 hours per day sleep indoor; 12 hours per day sitting, awake indoor (office, home); 3 hours per day light exercise outdoor (commuting, lunch walk); 1 hour per day heavy exercise outdoor (sport).

It will be apparent from the above that different scenarios for future actions of the subject can be simulated to predict a future accumulated amount for different scenarios (e.g. less time spent exercising, less time spent outdoors, increased time spent outdoors with a face mask and so on).

In some embodiments, calculation of the dosage of the air pollutant deposited in the portion of subject's respiratory tract is based on the inhalation and exhalation flow rate. In particular, the inhalation and exhalation rate can be processed to determine, with more precision, how much air pollutant is leaving the subject's respiratory tract and thereby more accurately determine the dosage of the air pollutant deposited.

Figure 5:
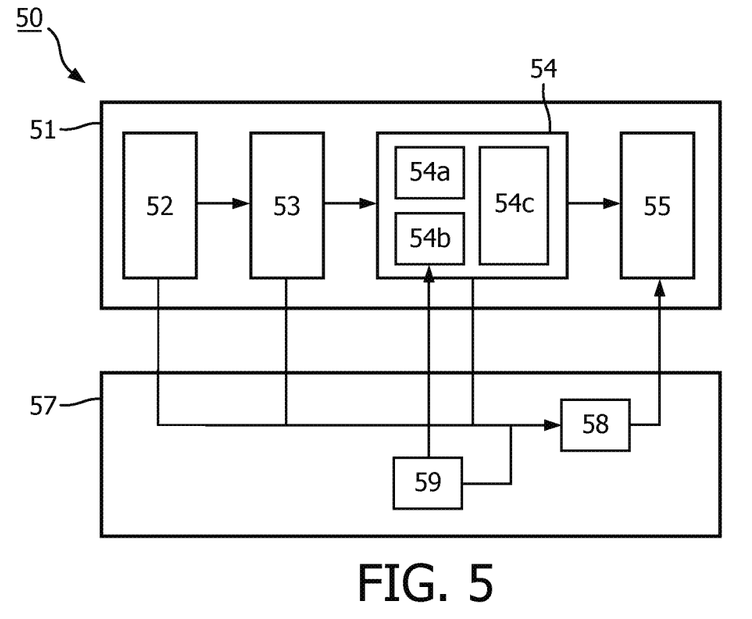
FIG. 5 illustrates a system according to an embodiment of the invention.

FIG. 5 illustrates a system 50 according to an embodiment.

The system is formed of a mobile device 51 and a remote server 57, such as a cloud-based computing service.

The mobile device 51 comprises a sensor system 52, a data processing unit 53, a dosage calculation unit 54 and a user interface 55. The remote server 57 comprises a risk calculation unit 58 and a data storage system 59.

The data processing unit 53 is adapted to determine an inhalation flow rate of the subject. The data processing unit 53 is also adapted to determine a pollution level representative of an amount of the air pollutant in the air inhaled by the subject during the predetermined time period. The data processing unit 53 is also adapted to obtain a model of the subject's respiratory tract.

The data processing unit 53 may receive sensor data from the sensor system 52 in order to perform its tasks. For example, the sensor system 52 may provide information on a respiration rate of the subject, which can be used to determine an inhalation flow rate. By way of another example, the sensor system 52 may provide environment information for modifying a pollution level, as previously described.

Thus, the sensor system 52 may comprise one or more of the following: a location sensor (e.g. employing GPS to locate the subject), an accelerometer, a microphone, a particle sensor, a vital sign sensor and/or a communication unit (e.g. to communicate with external sensors, such as an external pollution level monitoring device).

The obtaining unit 54 comprises a dosage calculation unit 54a adapted to determine an amount of the air pollutant that is deposited in the subject's respiratory tract during a predetermined time period, i.e. a dosage of the air pollutant. Preferably, the dosage calculation unit 54a performs this determination using the inhalation flow rate, the pollution level and the model of the subject's respiratory tract obtained by the data processing unit 53. Methods of performing such a calculation have previously been described.

The obtaining unit 54 also comprises a historic information obtainer 54b adapted to obtain historic information representative of the amount of the air pollutant cumulatively deposited in the subject's respiratory tract before the predetermined time period. The historic information obtainer 54b may obtain this information, for example, from the data storage system 59 or it may estimate the historic information using the dosage calculated by the dosage calculation unit 54a.

The obtaining unit also comprises an accumulative amount determiner 54c, adapted to determine an accumulative amount of the target air pollutant deposited in the subjects' respiratory tract, based on the dosage and the historic information. This may be performed using any previously described method.

The risk calculation unit 58 is adapted to calculate a risk level based on the determined dosage of the air pollutant and the historic information (e.g. based on the accumulative amount determined by the accumulative amount determiner), so that the risk level represents an amount of risk to the subject's health resulting from the accumulated deposition of the air pollutant in the subject's respiratory tract.

The user interface 55 is adapted to display the risk level calculated by the risk calculation unit for viewing by the subject and/or a clinician. The level of detail of the risk level displayed can vary depending upon the target audience for the risk level. The subject in question may be given a simplified overview of the risk level (for ease of understanding), whilst a clinician may be given a more detailed overview. For example, the view for a subject can include a single score, while a view for the clinician can include a risk score per disease, also including the confidence interval for each of these scores.

The risk calculation unit 58 may be adapted to determine a risk level further based on, for example, health data of the subject. Health data of the subject may be stored in the data storage system 59.

Of course, in some embodiments, the risk calculation unit 58 may be disposed in the mobile device 51. In some embodiments, the data processing unit 53 and/or dosage calculation unit 54 is instead disposed in the remote server 57. Thus, the different units of the mobile device 51 and the remote server 57 may be interchanged between the two.

Figure 6:
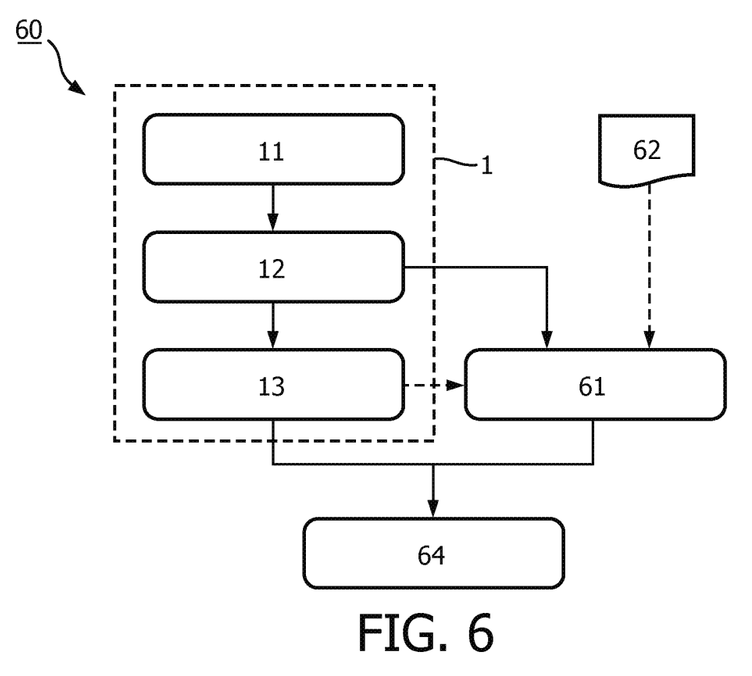
FIG. 6 illustrates a method according to an embodiment.

FIG. 6 illustrates a method 60 according to various embodiments described herein. The method 60 is adapted to generate a risk mitigation strategy for the subject.

The method 60 comprises a process 1 of determining a risk level of the subject. This may be performed by carrying out any previously described method.

The method 60 also comprises a step 61 of generating a risk mitigation strategy for the subject based on at least determined dosage of the air pollutant and the historic information, so that a generated risk mitigation strategy represents a strategy for reducing a risk caused by the accumulation of the air pollutant in the subject's respiratory tract.

The method 60 may further comprise a step 64 of displaying the risk mitigation strategy (and optionally the determined risk level) for viewing by the subject or a clinician, for example, via a user interface.

Step 61 may, for example, comprise determining a current accumulated amount of the target pollutant in the subject's respiratory system and processing the current accumulated amount with a machine learning model to identify a risk mitigation strategy.

The machine learning model can define a relationship between current accumulated amount and risk mitigation strategies (i.e. to ensure that future accumulation of the air pollutant doesn't result in an increased risk to the subject).

Methods of generating a machine learning model will be well known to the skilled person. Typically, this comprises obtaining training data comprising example input data (here: current accumulated amount) and example output data (here: risk mitigation strategy), generating estimated output data by processing the example input data with a machine learning model (e.g. initialized with random parameter values) and modifying the machine learning model to minimize the difference between the estimated output data and the example output data.

In this way, personalized feedback can be provided to the subject based on their personal health status—i.e. the accumulated amount of the target air pollutant in their respiratory tract.

In another example, step 61 comprises identifying a risk mitigation strategy based on known associations between accumulated amount of pollutant and subject characteristics or information.

For example, a regression analysis can be used to identify associations between accumulated amount of pollutant deposited in a subject's respiratory tract and subject information (such as location of subject, breathing rate of subject, fitness of subject and so on). To identify relevant associations, a regression analysis may be performed on a training dataset, each entry of which associates accumulated amount of pollutant in a historic subject's respiratory tract to subject information of the historic subject. In this way, the regression analysis can learn associations between accumulated amount of pollutant and subject information.

The associations may then be used to determine methods for minimizing a risk in the subject, based on the accumulated amount of pollutant deposited in their respiratory tract (e.g. increasing/reducing exercise).

Preferably, step 61 comprises obtaining subject information 62 comprising information about the subject, such as health data or subject characteristics (e.g. age, gender, weight etc.). The machine learning model may be adapted to receive, as input data, the current accumulated amount and the subject information and determine a risk mitigation strategy based on the input data.

In some embodiments, a predicted value for a future accumulated amount is determined based on an assumption that the subject follows the risk mitigation strategy. A risk value, based on the predicted future accumulated amount, may be determined (e.g. following any previously, identified method) and is optionally presented to the subject. This increases a likelihood that the subject will follow the risk mitigation strategy Examples of risk mitigation strategies include: minimizing exposure to the air pollutant in an outdoors environment (e.g. by taking a different commuting route); recommending cooking using alternative means (e.g. to reduce pollutants caused by certain cooking systems); spending more time indoors and so on.

In further embodiments, step 61 comprises obtaining the risk level of the subject (i.e. from step 13) and determining a risk mitigation strategy further based on the risk level.

Embodiments may be adapted wherein the amount of the air pollutant deposited in the subject's respiratory tract over a predetermined time period is replaced by the amount of the air pollutant absorbed into the subject's blood stream. It will be appreciated that only a proportion of the pollutant deposited in the subject's respiratory tract will be absorbed into the subject's blood stream. Thus, a more accurate representation of the potential risk to the subject can be calculated.

Where embodiments constitute a method, it should be understood that such a method may be a process for execution by a computer, i.e. may be a computer-implementable method. The various steps of the method may therefore reflect various parts of a computer program, e.g. various parts of one or more algorithms, or various modules/units of a system for carrying out a method. In particular, a system may be a single device or a collection of distributed devices that are adapted to execute one or more embodiments.

As discussed above, embodiments make use of a system. The system can be implemented in numerous ways, with software and/or hardware, to perform the various functions required. A processor is one example of a system which employs one or more microprocessors that may be programmed using software (e.g., microcode) to perform the required functions. A system may however be implemented with or without employing a processor, and also may be implemented as a combination of dedicated hardware to perform some functions and a processor (e.g., one or more programmed microprocessors and associated circuitry) to perform other functions.

Examples of system components that may be employed in various embodiments of the present disclosure include, but are not limited to, conventional microprocessors, application specific integrated circuits (ASICs), and field-programmable gate arrays (FPGAs).

In various implementations, a processor or system may be associated with one or more storage media such as volatile and non-volatile computer memory such as RAM, PROM, EPROM, and EEPROM. The storage media may be encoded with one or more programs that, when executed on one or more processors and/or systems, perform the required functions. Various storage media may be fixed within a processor or system or may be transportable, such that the one or more programs stored thereon can be loaded into a processor or system.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for determining a risk level an air pollutant poses to a subject's health, the method comprising:
   determining a dosage of the air pollutant received by the subject, the dosage representing an amount of the air pollutant deposited in a portion of the subject's respiratory tract over a predetermined time period;
   obtaining historic information representative of the amount of the air pollutant cumulatively deposited in the subject's respiratory tract before the predetermined time period; and
   calculating a risk level based on the determined dosage of the air pollutant and the historic information, so that the risk level represents an amount of risk to the subject's health resulting from the accumulated deposition of the air pollutant in the subject's respiratory tract,
   wherein determining the dosage of the air pollutant comprises:
   determining an inhalation and/or exhalation flow rate of the subject;
   obtaining a pollution level representative of an amount of the air pollutant in the air inhaled by the subject during the predetermined time period;
   obtaining a model of the portion of the subject's respiratory tract; and
   determining a dosage of the air pollutant deposited in the portion of the subject's respiratory tract over the predetermined time period based on the inhalation and/or exhalation flow rate, the pollution level and the model of the portion of the subject's respiratory tract.

2. The method of claim 1, wherein the step of calculating a risk level based on the determined dosage of the air pollutant and the historic information comprises:
   estimating an current accumulative amount of air pollutant deposited in the subject's respiratory tract at the end of the predetermined period based on the determined dosage of the air pollutant and the historic information; and
   calculating a risk level based on the estimated current accumulated amount of air pollutant.

3. The method of claim 1, wherein the step of calculating a risk level based on the determined dosage of the air pollutant and the historic information comprises:
   predicting a future accumulative amount of air pollutant deposited in the portion of the subject's respiratory tract a future point in time, based on the determined dosage of the air pollutant and the historic information; and
   calculating a risk level based on the predicted future accumulated amount of air pollutant.

4. The method of claim 1, wherein the step of calculating a risk level comprises:
   modelling an accumulated amount of air pollutant deposited in the respiratory tract of the subject over time using the determined dosage of the air pollutant and the historic information; and
   using the model to determine the risk level of the subject.

5. The method of claim 1, wherein the step of calculating a risk level comprises:

obtaining comparative amount information representing the accumulated amount of the target air pollutant in at least one other subject; and determining a risk level of the subject further based on the comparative amount information.

6. The method of claim 1, wherein the step of obtaining a pollution level comprises:

determining a location of the subject;

obtaining, based on the location of the subject, air pollution data indicative of an amount of the air pollutant in outdoor air at the location of the subject;

obtaining environment information indicative of one or more characteristics of an environment in the vicinity of the subject; and modifying the air pollution data based on the environment information to thereby determine an environment specific pollution level representative of an amount of the air pollutant in the air inhaled by the subject.

7. The method of claim 1, wherein the step of determining an inhalation and/or exhalation flow rate comprises:

determining a lung capacity of the subject;

determining a respiration rate of the subject; and determining an inhalation flow rate based on the lung capacity and respiration rate of the subject.

8. The method of claim 1, wherein the step of determining an inhalation and/or exhalation flow rate comprises:

obtaining sensor data from a mobile device associated with the subject; determining an activity performed by the subject based on the sensor data; and determining an inhalation flow rate based on the determined activity performed by the subject.

9. The method of claim 1, wherein:

the step of obtaining a model of the portion of the subject's respiratory tract comprises obtaining a multiple-path particle dosimetry model of the portion of the subject's respiratory tract; and the step of determining a dosage of the air pollutant deposited in the portion of the subjects respiratory tract over the predetermined period of time comprises using the multiple-path dosimetry model to process the inhalation and/or exhalation flow rate and pollution level to thereby determine a dosage of the air pollutant.

10. The method of claim 1, further comprising generating a risk mitigation strategy for the subject based on at least determined dosage of the air pollutant and the historic information, so that a generated risk mitigation strategy represents a strategy for reducing a risk caused by the accumulation of the air pollutant in the portion of the subject's respiratory tract.

11. The method of claim 1, further comprising a step of displaying the risk level to the subject.

12. A computer program comprising code means for implementing the method of claim 1 when said program is run on a computer.

13. A system for determining a risk level an air pollutant poses to a subject's health, the system comprising:

an obtaining unit comprising a processor and a non-transitory computer-readable medium configured to execute and store, respectively, a set of computer-readable instructions that when executed by the processor are configured to:

determine a dosage of the air pollutant received by the subject, the dosage representing an amount of the air pollutant deposited in a portion of the subject's respiratory tract over a predetermined time period, wherein determining the dosage of the air pollutant comprises:

determining an inhalation and/or exhalation flow rate of the subject;

obtaining a pollution level representative of an amount of the air pollutant in the air inhaled by the subject during the predetermined time period;

obtaining a model of the portion of the subject's respiratory tract; and determining a dosage of the air pollutant deposited in the portion of the subject's respiratory tract over the predetermined time period based on the inhalation and/or exhalation flow rate, the pollution level and the model of the portion of the subject's respiratory tract;

obtain historic information representative of the amount of the air pollutant cumulatively deposited in the portion of the subject's respiratory tract before the predetermined time period; and a risk calculation unit comprising a processor and non-transitory computer-readable medium configured to execute and store, respectively, a set of computer-readable instructions that when executed by the processor are configured to calculate a risk level based on the determined dosage of the air pollutant and the historic information, so that the risk level represents an amount of risk to the subject's health resulting from the accumulated deposition of the air pollutant in the portion of the subject's respiratory tract.

14. The system of claim 13, wherein:

the obtaining unit is adapted to estimate an current accumulative amount of air pollutant deposited in the portion of the subject's respiratory tract at the end of the predetermined time period based on the determined dosage of the air pollutant and the historic information; and the risk calculation unit is adapted to calculating a risk level based on the estimated current accumulated amount of air pollutant.

* * * * *